United States Patent [19]

Alfranseder et al.

[11] 4,335,014
[45] Jun. 15, 1982

[54] PROCESS FOR IMPROVING THE ACTIVITY OF SUPPORTED SILVER CATALYSTS

[75] Inventors: Josef Alfranseder, Marktl; Sigmund Mayer, Burgkirchen; Siegfried Rebsdat, Burg; Josef Riedl, Burgkirchen; Iwo Schaffelhofer, Burghausen, all of Fed. Rep. of Germany

[73] Assignee: Hoechst Aktiengesellschaft, Frankfurt, Fed. Rep. of Germany

[21] Appl. No.: 188,237

[22] Filed: Sep. 17, 1980

[30] Foreign Application Priority Data

Sep. 21, 1979 [DE] Fed. Rep. of Germany ....... 2938245

[51] Int. Cl.$^3$ .......................... B01J 23/96; B01J 23/48
[52] U.S. Cl. ..................................... 252/412; 252/414; 252/476; 549/534; 549/538
[58] Field of Search ....................... 252/412, 414, 476; 260/348.34

[56] References Cited

U.S. PATENT DOCUMENTS

| | | | |
|---|---|---|---|
| 4,123,385 | 10/1978 | Rebsdat et al. ..................... | 252/412 |
| 4,125,480 | 11/1978 | Maxwell .............................. | 252/412 |
| 4,278,562 | 7/1981 | Mross et al. ........................ | 252/476 |

FOREIGN PATENT DOCUMENTS

| | | | |
|---|---|---|---|
| 1078 | 8/1978 | European Pat. Off. ....... | 260/348.34 |
| 773815 | 5/1957 | United Kingdom ................ | 252/412 |

*Primary Examiner*—P. E. Konopka
*Attorney, Agent, or Firm*—Connolly and Hutz

[57] ABSTRACT

Supported silver catalysts, which should have as high an activity as possible, are employed for the manufacture of ethylene oxide by oxidizing ethylene by means of oxygen or air. A process is described for improving the activity of supported silver catalysts which have already been used, in which the used catalyst is first washed with an inert liquid containing ammonia and/or aliphatic amines and 1 to 1,000 parts, per 1 million parts of catalyst, of cesium, rubidium or a mixture thereof is then deposited on the washed catalyst. The deposition is generally effected with the aid of an impregnating solution containing the cesium and/or rubidium compounds in a suitable quantity. This process makes it possible to improve considerably the activity of supported silver catalysts which have already been in use for the oxidation of ethylene by means of oxygen or air.

2 Claims, No Drawings

PROCESS FOR IMPROVING THE ACTIVITY OF SUPPORTED SILVER CATALYSTS

The invention relates to a process for improving the activity of supported silver catalysts for the direct oxidation of ethylene to ethylene oxide by means of molecular oxygen or air.

Silver catalysts, the manufacture of which has been known for a long time and has been described in a variety of patent specifications, are employed for the manufacture of ethylene oxide by the oxidation of ethylene by means of oxygen or air. A whole series of large-scale industrial plants for the manufacture of ethylene oxide use the silver catalyst process. In this process, it is customary only to react a fraction of the ethylene employed. On the supporting material, impregnated with silver, the ethylene which is reacted is converted by means of oxygen predominantly into ethylene oxide; the remainder is transformed virtually completely into carbon dioxide and water.

In the course of time, a very wide variety of silver catalysts has been developed, specifically with the aim of increasing the selectivity in respect of the preferred formation of ethylene oxide and of repressing the formation of $CO_2$ and water.

With rising prices of raw materials and increasing scarcity of raw materials, increased selectivity of catalysts acquires a particular economic importance. In principle, two routes which enable supported silver catalysts having an increased selectivity to be obtained have been described in the literature in recent years. One route is based on the development of new supported silver catalysts which differ from the older catalysts particularly in the silver deposited having a special morphology, in a special support material or in selected promoters. For example, German Offenlegungsschrift No. 2,300,512 describes a supported silver catalyst which is obtained by depositing on aluminum oxide from an aqueous solution, simultaneously with the silver, 0.0004 to 0.0027 g equivalents of a potassium, rubidium or cesium compound per kg of catalyst.

The other route for the preparation of supported silver catalysts having an increased selectivity is based on the fact that the selectivity of a catalyst which is in itself ready for use is substantially improved by an aftertreatment. In this route, the starting material is a supported silver catalyst which has already been utilized for the manufacture of ethylene oxide for periods of varying length. Such processes for improving selectivity are described in German Patent Specifications Nos. 2,519,599, 2,611,856 and 2,636,680, in German Auslegeschriften No. 2,649,359 and 2,740,480 and in German Offenlegungsschriften Nos. 2,712,785, 2,746,976 and No. 2,751,767. In the process of German Auslegeschrift No. 2,740,480, the activity of supported silver catalysts is improved by washing a catalyst which has already been used for the direct oxidation process with an inert liquid and then depositing on the catalyst 1 to 1,000 parts, per 1 million parts of catalyst, of cesium, rubidium or a mixture thereof.

It has now been found that it is possible to achieve a further improvement of activity in this known process if an inert liquid containing dissolved ammonia and/or aliphatic amines is used.

What has been found is, therefore, a process for improving the activity of supported silver catalysts for the direct oxidation of ethylene to ethylene oxide by means of molecular oxygen or air, the catalyst which has been used for direct oxidation being washed with a liquid which is inert (towards the catalysts) and 1 to 1,000 parts, per 1 million parts of catalyst, of cesium, rubidium or a mixture thereof then being deposited on the catalyst, wherein an inert liquid containing dissolved ammonia and/or aliphatic amines is used for the washing process.

The proportion of ammonia, aliphatic amines or mixtures thereof in the inert liquid can vary within wide limits; in general, relatively dilute solutions are used. The concentration of ammonia and/or aliphatic amine is appropriately 0.1 to 25% by weight, preferably 1 to 10% by weight, relative to the solution (weight of the whole solution).

The aliphatic amines within the scope of the invention can be monoamines, diamines or polyamines, preferably containing 2 to 8 C atoms. Preferred monoamines are monoalkylamines, dialkylamines or trialkylamines, such as ethylamine, propylamine, isopropylamine, butylamine, secondary butylamine, isobutylamine, diethylamine, dipropylamine and dibutylamine; and alkanolamines, such as monoethanolamine, monopropanolamine, monobutanolamine and diethanolamine. Preferred diamines and polyamines are 1,2-diaminoethane (ethylenediamine), 1,2-diaminopropane, 1,3-diaminopropane, 1,4-diaminobutane and diethylenetriamine.

The inorganic or organic wash liquids described in German Offenlegungsschrift No. 2,740,480 can be used as the inert liquids to which ammonia and/or an aliphatic amine is added in accordance with the invention. Preferred inert liquids within the scope of the present invention are aliphatic ketones having 3 to 10, preferably 3 to 6, C atoms, such as acetone, ethyl propyl ketone, methyl ethyl ketone, diethyl ketone and dipropyl ketone; aliphatic alcohols having 1 to 6, preferably 1 to 3, C atoms, such as methanol, ethanol, propanol and isopropanol; water; and mixtures of these liquids.

If aliphatic amines are added in accordance with the invention, it is appropriate for the solvent to be a mixture of alcohol and/or a ketone and water. Wash solutions of this type preferably consist of propylamine, butylamine, secondary butylamine, monoethanolamine or ethylenediamine in a quantity of 1 to 20% by weight, water in a quantity of 10 to 50% by weight and alcohol or ketone in a quantity of 30 to 89% by weight, the percentages by weight being in each case relative to the solution; these solutions can optionally also additionally contain ammonia in a quantity of up to 10% by weight, relative to the solution.

In accordance with the invention, the following wash solutions are preferred:

(a) aqueous ammonia solutions or alcoholic ammonia solutions having an $NH_3$ concentration of 1 to 10% by weight, relative to the solution; or (b) aqueous alcoholic ammonia solutions or aqueous ketonic ammonia solutions having an $NH_3$ concentration of 1 to 10% by weight, a water concentration of 10 to 50% by weight and an alcohol or ketone concentration of 40 to 89% by weight, percentages being in each case relative to the solution.

What has been stated in German Offenlegungsschrift No. 2,740,480 also applies in respect of washing the used supported silver catalyst in the process according to the invention. Thus the used catalyst can be washed in a variety of procedures with the solution to be used in accordance with the invention. It is only necessary that the catalyst should come into contact with the wash liquid and should subsequently be separated therefrom. It is also possible to repeat several times the washing of the catalyst with the wash liquid. The percentage composition in respect of amine, NH3 and solvent can be varied. The time within which the catalyst is in contact with the wash liquid is not critical; it can vary from a few minutes up to several hours or days and is generally 5 minutes to 5 days, preferably 0.5 to 10 hours, especially 1 to 3 hours. The washing can be carried out, for example, by covering the catalyst in a container with the wash liquid and then separating it from the wash liquid by filtration, filtration with suction or decantation. It is appropriate to repeat the washing process several times, preferably 2 to 3 times, using a fresh (new) was liquid each time.

Besides the procedure described, it is also possible to effect the washing by pouring the wash liquid over the catalyst, arranged, for example, as a fixed bed in one or more tubes, the wash liquid being poured in at one end of the tubes and allowed to run out at the other end of the tubes. This washing process can also be repeated several times and is preferably carried out 1 to 5 times, it being appropriate to employ a fresh (not yet used) wash liquid each time. It can be advantageous, when pouring the wash liquid over the catalyst (once or several times), not to allow the wash liquid to run off immediately, but to leave it in the tube or tubes for some time, preferably for 0.5 to 48 hours, after which the outlet is released. It is not necessary to wash the whole of the used catalyst. The effect desired within the scope of the invention can also be achieved even if only a part, for example 30 to 50%, of the (total amount present of the) used catalyst is washed. The quantity of wash liquid depends on the quantity of catalyst to be washed and should, of course, be such that the catalyst comes into contact with the liquid. The quantity of wash liquid (per washing process) in parts by weight or parts by volume is appropriately at least about ⅓ of the quantity, in % by volume, of catalyst to be washed; it is preferable to employ equal quantities up to 5-fold quantities, especially 2 to 3-fold quantities, of wash liquid. If washing is carried out several times, for example using an aqueous alcoholic or aqueous ketonic solution of ammonia and/or amine, it has proved advantageous to reduce the concentration of ammonia and/or amine progressively and/or to increase the quantity of alcohol and/or of ketone. Such washing has the effect of removing also a large part of the water from the catalyst and of facilitating the drying of the catalyst. The temperature of the catalyst and of the wash liquid during washing is not critical and is determined rather by practical considerations. It is appropriately below the boiling point of the inert liquid used and of the amine which may be employed. If ammonia is added, temperatures of 15° to 30° C. are appropriate. Possible evaporation of the inert liquid, for example the alcohol, or emission as gas of the ammonia or amine can be prevented by the application of pressure. In this case, the pressure is appropriately 1 to 20 bars, preferably 1 to 5 bars.

After washing, the deposition of 1 to 1,000 mg, per kg of catalyst, of cesium, rubidium or a mixture of the two (any desired ratio being possible) is effected in accordance with the invention. In this respect, essentially what has been stated in German Auslegeschrift No. 2,740,480, from column 5 onwards, also applies in the case of the process according to the invention. The deposition of cesium and/or rubidium on the washed catalyst, the second process stage in the process according to the invention, can be carried out directly after the first process stage, the washing, or only after the catalyst has been subjected to drying, residues of liquid which may have remained from the washing, after separation from the wash liquid, being removed. Drying can be achieved, for example, by passing an inert gas through the catalyst and/or by warming the catalyst, and a reduced pressure can also be applied in order to accelerate the drying process. The temperature used in the warming process is not critical; it depends on the wash liquid employed and, if drying is carried out at atmospheric pressure, it will correspond approximately to the boiling point of the wash liquid. Examples of appropriate drying temperatures are about 20° to 250° C., preferably 50° to 150° C. If drying is carried out at a reduced pressure, complete evaporation of the wash liquid remaining on the catalyst, after the bulk of it has already been removed, can also be achieved even at room temperature, that is to say at 15° to 25° C. or, for example, at 25° to 80° C. Drying is also accelerated by warming and simultaneously passing an inert gas over the catalyst. Non-combustible gases which do not support combustion, such as nitrogen or carbon dioxide, are appropriately used as the inert gas. If sources of ignition are excluded and/or if a large excess of the gas is used, which does not form ignitable mixtures with the volatile substances, it is also possible to use other gases, in particular air.

Various procedures can be selected for depositing cesium and/or rubidium on the washed (dried or not dried) catalyst; the only important factor is that the indicated quantities of cesium, rubidium or mixtures thereof are deposited on the catalyst (specifically on the whole of the used catalyst, that is to say also on partial quantities which may not have been washed).

The deposition of cesium and/or rubidium is appropriately effected by wetting (immersing or impregnating) the catalyst with an impregnating liquid containing one or more compounds of cesium and/or rubidium.

The impregnating liquid should contain the cesium and/or rubidium compounds in as finely divided a form as possible. The said compounds can be in the form of a dispersion or emulsion, but preferably they are applied in a dissolved form (an impregnating solution). The inorganic and organic, inert liquids described above can be used as the solvent or as the liquid phase of a dispersion or emulsion. Preferred solvents are aliphatic, alicyclic or aromatic ketones, preferably aliphatic ketones having 3 to 10 C atoms, such as acetone, methyl ethyl ketone or ethyl propyl ketone; and aliphatic, alicyclic or aromatic alcohols, preferably aliphatic or alicyclic alcohols having 1 to 6 atoms. Aliphatic (straightchain or branched) alcohols having 1 to 6 C atoms, especially those having 1 to 3 C atoms, such as methanol, ethanol, propanol or isopropanol, are particularly preferred. The organic solvents can be employed on their own (mixtures with one another are also possible) or can be employed mixed with water. Pure water can also be used as the solvent. If mixtures of organic solvents and water are employed, preferred mixtures are those having a water content of up to 40% by weight, preferably up to 20% by weight, relative to the total liquid.

The nature of the cesium and/or rubidium compounds is not decisive for the effect according to the invention. As a rule, the compound selected or the compounds selected contain cesium and rubidium in the form of the corresponding cations. The radical (anion)

with which the cesium and/or rubidium is combined is of little importance. Inorganic or organic radicals are suitable. However, this radical should not consist of substances which, particularly after treatment with the gaseous reaction mixture for the manufacture of ethylene oxide, act as a so-called catalyst poison. The following are suitable cesium and rubidium compounds: inorganic compounds, preferably inorganic salts, for example sulfates, nitrites, nitrates, silicates, carbonates or bicarbonates; hydroxides and oxides; organic compounds, preferably organic salts, for example formates, acetates, oxalates, malonates, succinates, butyrates, laurates, stearates, lactates, tartrates and benzoates; and alcoholates, for example methylates, ethylates and phenates. It is preferable to employ inorganic or organic salts, particularly the formates, acetates, carbonates, bicarbonates or nitrates; the hydroxides; and the alcoholates of aliphatic alcohols which preferably have 1 to 6, particularly 1 to 3, C atoms. Either one or more cesium or rubidium compounds can be employed; mixtures of cesium and rubidium compounds are also suitable.

The concentration of the cesium and/or rubidium compounds in the impregnating liquid is not critical; in general, it will depend on the solubility of the compounds. The only decisive factor is that, after the catalyst has been treated with the impregnating liquid, a concentration of 1 to 1,000 mg/kg of cesium and/or rubidium should be set up on the catalyst (the concentration figure for cesium or rubidium on the catalyst relates only to the cesium or rubidium metal, no account is taken in this figure of the radical in the compound selected). It is advisable to take a minimum concentration of 0.0003% by weight of cesium and/or rubidium in the impregnating liquid (impregnating solution). A concentration of 0.003 to 1.0% by weight, preferably 0.005 to 0.5% by weight, of cesium and/or rubidium compound, relative to the impregnating solution, has proved particularly appropriate. However, the guiding factor in adjusting the concentration of the impregnating solution is always the desired concentration of rubidium or cesium on the catalyst.

The quantity of impregnating liquid can also be varied within wide limits. In this respect, the guiding factor will be the quantity of catalyst to be treated, so that all the catalyst particles are also wetted completely. No upper limit is therefore set to the quantity of impregnating liquid by its action. In general, 75 to 150% by volume of impregnating liquid, relative to the catalyst to be treated, will be taken.

The treatment of the washed catalyst with the impregnating liquid, in order to deposit 1 to 1,000 mg/kg, preferably 3 to 300 mg/kg, of cesium and/or rubidium on the catalyst, can be carried out by a variety of procedures. Suitable processes are described in German Auslegeschrift No. 2,740,480. An appropriate procedure is immersion (wetting or impregnation), the impregnating liquid being poured over the catalyst and the excess portion of the liquid being separated off (by decantation or simply allowing it to drain). This is carried out, for example, in a container, if appropriate while stirring, or on the catalyst arranged as a fixed bed in one or more tubes. This latter method is particularly advisable in large plants in which the catalyst is already present in the tubes of the reactor. The pouring over (flooding) can be carried out once or several times (using the impregnating liquid which has been separated off or using a freshly prepared impregnating liquid).

The deposition of 1 to 1,000 parts, preferably 3 to 300 parts, of cesium and/or rubidium, per 1 million parts of catalyst, on the washed catalyst can also be effected in two or more stages (separated by an interval of time), preferably two to five stages, the catalyst being re-employed for the direct oxidation of ethylene to ethylene oxide by means of molecular oxygen or air, after each treatment stage. The deferment in terms of time between the individual treatment stages, that is to say the time interval during which the catalyst has been re-employed for direct oxidation after a treatment, can vary within wide limits; it is appropriately one week up to several months, preferably 1 to 20 weeks, particularly 3 to 5 weeks. The upper limit of the time interval is limited more by techno-economic considerations and the lower limit is appropriately not less than one hour. The quantity of cesium and/or rubidium which is deposited on the washed catalyst per treatment stage can be varied within the range from 1 to 1,000 mg/kg, preferably 3 to 300 mg/kg. As a rule, at least 1 mg/kg, preferably 3 to 100 mg/kg will be deposited on the catalyst in the first treatment stage and the same quantity or a fraction thereof will be deposited in each of the following treatment stages.

After the washed catalyst has been treated with the impregnating liquid (in accordance with one of the methods just described), it is appropriate if any residues of liquid which may have remained after the separation of the bulk of the impregnating liquid on the catalyst are removed, which can be effected by one of the drying processes described above. The temperatures which may be used for this in a given case depend, similarly, on the impregnating liquid to be removed (to be vaporized) and are 50° to 250° C., preferably 50° to 150° C., particularly 70° to 120° C.

The process according to the invention is independent of the nature (for example the composition, buildup or structure) of the silver catalyst itself. Any silver catalyst which is suitable for the direct oxidation of ethylene to ethylene oxide by means of molecular oxygen or air can be used in the process according to the invention. Silver catalysts for the direct oxidation of ethylene to ethylene oxide by means of molecular oxygen or air are described exhaustively in the literature, as is the direct oxidation process itself, for example in the following U.S. Pat. Nos. 2,615,899, 3,899,445 and No. 3,962,136.

The silver catalysts in question generally consist of 1 to 40% by weight (relative to the total catalyst) of silver on a supporting material and optionally of quantities of varying amounts of a very wide variety of promotors or co-activators. In these catalysts, the silver is deposited in the form of metal on the internal and external surfaces of the, preferably porous, supporting material and is distributed over the whole surface thereof as uniformly as possible. The morphology of the silver deposited on the supporting material can vary within wide limits. In general, it has the form of spherical particles having a diameter of 0.01 to 10$\mu$. The supporting material appropriately consists of porous, heat-resistant materials which remain inert under the conditions occurring in the direct oxidation of ethylene. Examples of such materials are aluminum compounds, preferably aluminum oxides of a very wide variety of structures, magnesium oxides, kieselguhr, pumice stone, silicon dioxide, silicon carbide, clays, corundum, zeolites, metal oxides and the like. Particularly preferred supporting materials are $\alpha$-aluminum oxides, since they have a largely uniform pore size. They are characterized in particular by their specific surface (m²/g), their specific pore volume (cm³/g) and their average pore size ($\mu$). The supporting materials are generally employed in the form of granules, spheres, small pieces, rings or the like.

The two-stage process according to the invention relates to used silver catalysts. In this context the expression "used" means that the catalyst has already been employed for the conversion of ethylene to ethylene oxide by means of molecular oxygen or air, and it is unimportant whether its original selectivity has declined or not. The timing during which the catalyst has been in use for the oxidation of ethylene to ethylene oxide, before the treatment according to the invention, can vary within wide limits; it can vary from a few weeks (1 to 3) to several years (1 to 10) or longer. In this regard, the activity of the catalyst can have declined, that is to say its selectivity can have fallen off (which generally takes place after a fairly long time of use), or the catalyst can also have retained its original selectivity.

The washing and deposition of cesium and/or rubidium according to the invention thus makes it possible to improve considerably the activity of supported silver catalysts which have already been in use for the direct oxidation of ethylene by means of molecular oxygen or air. The activity of a catalyst can be expressed as the conversion (in %) of ethylene at a given temperature or as the molar ratio of ethylene converted into ethylene oxide, that is, its selectivity. A catalyst is the more active, the more ethylene is converted at a specific temperature, the higher the selectivity is at a specific conversion and the lower the temperature is in order to achieve a specific conversion.

The process according to the invention increases considerably, not only the selectivity of used supported silver catalysts, but also the conversion. With catalysts which have been treated in accordance with the invention, it is also possible, in addition, to reduce the reaction temperature—at the same, or even a higher, conversion. This is particularly significant, because, at a lower reaction temperature, the formation of undesirable by-products, such as carbon dioxide, formaldehyde or acetaldehyde, is considerably repressed. In view of the large quantities of ethylene oxide which are produced by the ethylene oxidation process, an increase in yield of only a few percent, or even of a tenth of a percent, acquires considerable economic importance. A factor which further distinguishes the process according to the invention is that it can be carried out in the conventional large-scale manufacturing plants (using the commercially available supported silver catalysts) without an appreciable additional outlay of energy, investment or materials.

The invention will now be illustrated in detail by means of examples.

The examples and comparison examples which follow are carried out in an experimental reactor consisting of a vertical reaction tube made of chrome-vanadium steel, having an internal width of 30 mm and a length of 300 mm. The reaction tube, which is provided with a jacket, is heated with hot oil which flows through the jacket. The reaction tube is filled to a depth of 200 mm with $\alpha$-Al₂O₃ pellets; this packing serves to preheat the feed gas. The catalyst to be tested rests on top of the inert packing. The feed gas enters the reaction tube (at normal pressure) from below and leaves it at the top.

The gas mixture employed consists of:

| | | | |
|---|---|---|---|
| $C_2H_4$ | 28% | by volume | |
| $CH_4$ | 53% | by volume | |
| $O_2$ | 8% | by volume | Gas mixture I |
| $CO_2$ | 5% | by volume | |
| $N_2$ | 6% | by volume | |
| Vinyl chloride | 0.0002% | by volume | (inhibitor) |
| or of: | | | |
| $C_2H_4$ | 4% | by volume | |
| $O_2$ | 5% | by volume | Gas mixture II |
| $CO_2$ | 4% | by volume | |
| $N_2$ | 87% | by volume. | |

The space-time velocity is:

$$250 \times \frac{\text{parts by volume of gas}}{\text{hours} \times \text{parts by volume of catalyst}}$$

The gas issuing at the reactor outlet is analyzed by gas chromatography and the conversion and selectivity are calculated. The temperature of the heat transfer medium is varied until a constant ethylene conversion of 7% is achieved in the case of gas mixture I, and of 35% in the case of gas mixture II. The time for which the tests are run is selected in such a way that there is no further change in the experimental values at the end. This is normally the case with a running time of 200 hours. Commercially available supported silver catalysts are employed for the tests. They consist of 10% of silver (particle size 1 to 5$\mu$) on $\alpha$-Al₂O₃ as the supporting material, which has the shape of rings with a length of 8 mm, an external diameter of 8 mm and an internal diameter of 2 mm—catalyst I—or the shape of cylinders with a diameter and a height of about 5 mm—catalyst II; the specific surface is 0.1 to 0.5 m²/g.

The cesium and/or rubidium content deposited on the catalyst is determined by atomic absorption spectroscopy (see the monograph: "Atomabsorptionsspektroskopie" ("Atomic Absorption Spectroscopy"), Bernhard Wells Verlag Chemie, 1972, page 114 et seq.). The determination is carried out in an air-acetylene flame and the Cs or Rb extinction is determined in emission.

EXAMPLE 1

50 g of the commercially available catalyst II described above, which has been employed for 4 years for the manufacture of ethylene oxide by direct oxidation of ethylene by means of oxygen, are covered at 20° C. in a 200 ml Erlenmeyer flask with a solution consisting of 25 ml of methanol, 10 ml of distilled water and 15 ml of a 25% strength aqueous ammonia solution and the mixture is allowed to stand for 10 hours. After the wash liquid has been decanted off, the catalyst is twice left to stand with methanol containing 10% of water, in each case for 0.5 hour, and the methanol is decanted off. The catalyst is then dried for 12 hours at 120° C. in a drying cabinet. The catalyst is cooled to 20° C. and 100 ml of a solution consisting of 50 ml of methanol, 1 g of distilled water and 0.02 g of cesium nitrate are poured over it and the mixture is allowed to stand for 1 hour at room temperature. After the impregnating solution has been decanted off, the catalyst is dried for 3 hours at 120° C. in a drying cabinet. The cesium concentration on the catalyst is 85 mg/kg.

The catalyst which has been treated in this way is now filled into the experimental reactor and is tested in the manner described with gas mixture I: the selectivity has risen from a previous figure of 68% at 7% ethylene conversion and a temperature of 260° C. to 75% at the same ethylene conversion, but at 227° C.

COMPARISON EXAMPLE 1

The procedure followed is as in Example 1, but the ammonia wash is omitted. This results in an increase in the selectivity from 68% at 260° C. to 71% at 250° C., at a constant conversion of 7% in each case.

EXAMPLE 2

50 g of the catalyst used in Example 1 are washed, as described above, four times with a wash liquid consisting of aqueous ammonia or of ammonia and isopropanol, in a 200 ml Erlenmeyer flask. The treatment time is in each case 2 hours at 30° C. The first wash is carried out with 50 ml of a 20% strength aqueous ammonia solution. The solution for the second wash consists of 25 ml of isopropyl alcohol, 10 ml of water and 15 ml of 25% strength aqueous ammonia. The solution for the third wash consists of 40 ml of isopropyl alcohol, 5 ml of water and 5 ml of 25% strength aqueous ammonia. The fourth wash is carried out with isopropyl alcohol. After the isopropyl alcohol (from the fourth wash) has been decanted off, a cesium solution, consisting of 50 ml of isopropanol, 5 g of water and 0.015 g of cesium acetate is poured over the catalyst, which is still wet, and the mixture is allowed to stand for 0.5 hour at 30° C. The impregnating solution is removed by filtration and the catalyst is dried for 20 hours at 150° C. in a drying cabinet. The cesium concentration is 70 mg/kg of catalyst. When tested with gas mixture I, the selectivity increases from a previous figure of 68% at 260° C. to 76% at 225° C.

COMPARISON EXAMPLE 2

The procedure followed is as in Example 2, but washing is carried out only three times with isopropanol containing 10% by weight of water, but no ammonia.

The selectivity rises from the previous figure of 68% at 260° C. to 72% at 245° C.

EXAMPLE 3

50 g of the catalyst II used in Example 1 are allowed to stand for 10 hours at 40° C. in a 200 ml Erlenmeyer flask together with a solution consisting of 40 ml of ethanol (denatured with butanone), 5 ml of water and 5 ml of ethylenediamine. After the wash liquid has been decanted off, the catalyst is washed with three times 100 ml of ethanol, the mixture being allowed to stand for 0.5 hour before decantation in each case. The washed catalyst is then dried for 24 hours at 170° C. The catalyst is cooled to 30° C. and is then immersed in a cesium solution as described in Example 1, for 1 hour. When tested on gas mixture II, the selectivity increases from 65% at 252° C. and 35% ethylene conversion to 73% at 237° C.

COMPARISON EXAMPLE 3

The procedure followed is as in Example 3, but the ethylenediamine is omitted. The selectivity increases from 65% at 252° C. to 68% at 245° C.

EXAMPLE 4

A solution consisting of 25 ml of methanol, 15 ml of water and 20 ml of 25% strength aqueous ammonia solution are poured over 50 g of catalyst I, which has been in use for 7 years for the manufacture of ethylene oxide by direct oxidation of ethylene by means of oxygen, in a 200 ml Erlenmeyer flask at 25° C., and the mixture is stirred gently for 5 hours. After the wash liquid has been removed by filtration, the catalyst is stirred, for 2 hours in each case, with twice 50 ml of methanol containing 10% by weight of water, after which the methanol is poured off. While still wet, the catalyst is then allowed to stand for 5 hours at 25° C. with 50 ml of an impregnating solution consisting of 1,000 mg of cesium nitrate and 1 kg of methanol. The impregnating solution is then poured off and the catalyst is dried for 24 hours at 150° C. in a drying cabinet. The cesium concentration on the catalyst is 130 mg/kg. When tested on gas mixture I, the selectivity increases from a previous figure of 66% at 7% ethylene conversion and 240° C. to 76% at the same ethylene conversion, but at 225° C.

COMPARISON EXAMPLE 4

The procedure followed is an in Example 4, but the ammonia is missing from the wash liquid. The selectivity increases from 66% at 240° C. to 75% at 225° C.

EXAMPLES 5 to 11

These examples are carried out analogously to Example 1 or 2, using the wash solutions and procedures indicated in the following table.

TABLE

| Example No. | Catalyst Type g | Gas mixture | 100 g of solvent consisting of | | | Treatment time at 20–30° C. hours | Cs impregnating solution | Reaction temperature °C. | Selectivity at 7% C₂H₄ conversion % |
|---|---|---|---|---|---|---|---|---|---|
| | | | % by weight of amine or ammonia | % by weight of H₂O | % by weight of alcohol or ketone | | | | |
| 5 | II 50 | 1 | sec.-butyl-amine 15 | 30 | acetone 55 | 10 | 350 mg Cs/kg of acetone | 227 | 76.5 |
| 6 | II 50 | 1 | ethylene-diamine 10 25% 10 strength NH₃ | 30 | methanol 50 | Twice for 2 hours | 300 mg Cs/kg of methanol | 226 | 77.2 |
| 7 | II 50 | 1 | mono-ethanol-amine 20 | 20 | isopropanol 60 | 3 times for 3 hours | 200 mg Cs/kg of isopropanol | 228 | 76.3 |
| 8 | II 50 | 1 | 25% 10 strength ammonia | 50 | acetone 40 | Twice for 2 hours | 400 mg Cs/kg of acetone | 225 | 76.3 |
| 9 | I 50 | 1 | diethan-olamine 20 | 50 | ethanol 30 (denatured with butanone) | Twice for 5 hours | 300 mg Cs/kg of methanol | 230 | 76.4 |

TABLE-continued

| Example No. | Catalyst Type g | Gas mixture | 100 g of solvent consisting of | | | Treatment time at 20–30° C. hours | Cs impregnating solution | Reaction temperature °C. | Selectivity at 7% C$_2$H$_4$ conversion % |
|---|---|---|---|---|---|---|---|---|---|
| | | | % by weight of amine or ammonia | % by weight of H$_2$O | % by weight of alcohol or ketone | | | | |
| 10 | 1 50 | 1 | 25% strength NH$_3$ 5 1,4-di-aminobutane 15 | 30 | methanol 50 | 24 | 700 mg Cs/kg of methanol | 228 | 77.5 |
| 11 | 1 50 | 1 | 25% strength NH$_3$ 2 sec.-butyl-amine 10 | 10 | methanol 50 acetone 28 | 24 | 300 mg Cs/kg of methanol | 227 | 76.8 |

We claim:
1. In the process for improving the activity of used supported silver catalysts used in the direct oxidation of ethylene to ethylene oxide by means of molecular oxygen or air in which the used catalyst is (a) firstly washed with an inert liquid and (b) on the washed catalyst is then deposited 1 to 1,000 parts, per 1 million parts of catalyst, of cesium, rubidium or a mixture thereof: the improvement which comprises using as said inert washing liquid a solution consisting of 10 to 50 percent by weight of water, 30 to 89 percent by weight of an aliphatic alcohol having 1 to 6 carbon atoms or an aliphatic ketone having 3 to 10 carbon atoms and 1 to 20 percent by weight of an amine selected from the group consisting of propylamine, butylamine, secondary butylamine, monoethanolamine, and ethylenediamine, the percentages by weight being in each case relative to the solution.

2. In the process for improving the activity of used supported silver catalyst used in the direct oxidation of ethylene to ethylene oxide by means of molecular oxygen or air in which the used catalyst is (a) firstly washed with an inert liquid and (b) on the washed catalyst is then deposited 1 to 1,000 parts, per 1 million parts of catalyst, of cesium, rubidium or a mixture thereof: the improvement which comprises using as said inert washing liquid a solution consisting of
(a) an aqueous ammonia solution or an alcoholic ammonia solution having an NH$_3$ concentration of 1 to 10 percent by weight; or
(b) an aqueous alcoholic ammonia solution or an aqueous ketonic ammonia solution having an NH$_3$ concentration of 1 to 10 percent by weight, a water concentration of 10 to 50 percent by weight and a concentration of alcohol or ketone of 40 to 89 percent by weight, the percentage by weight in each case relating to the solution; the alcohol in (a) and (b) being an aliphatic alcohol having 1 to 6 carbon atoms and the ketone in (b) being an aliphatic ketone having 3 to 10 carbon atoms.

* * * * *